United States Patent
Brown et al.

(10) Patent No.: US 11,026,644 B2
(45) Date of Patent: Jun. 8, 2021

(54) SYSTEM AND METHOD FOR NAVIGATING WITHIN THE LUNG

(71) Applicant: COVIDIEN LP, Mansfield, MA (US)

(72) Inventors: Andrew E. Brown, St. Paul, MN (US); David J. Miel, Minneapolis, MN (US); Matthew W. Baker, Edina, MN (US); Dorian Averbuch, Ramat Hasharon (IL); Eyal Klein, Tel Aviv (IL); Oren P. Weingarten, Hod Hasharon (IL)

(73) Assignee: COVIDIEN LP, Mansfield, MA (US)

( * ) Notice: Subject to any disclaimer, the term of this patent is extended or adjusted under 35 U.S.C. 154(b) by 97 days.

(21) Appl. No.: 15/714,412

(22) Filed: Sep. 25, 2017

(65) Prior Publication Data

US 2018/0008212 A1 Jan. 11, 2018

Related U.S. Application Data

(63) Continuation of application No. 14/753,288, filed on Jun. 29, 2015, now Pat. No. 9,770,216.

(Continued)

(51) Int. Cl.
*A61B 6/12* (2006.01)
*A61B 6/03* (2006.01)
(Continued)

(52) U.S. Cl.
CPC .............. *A61B 6/12* (2013.01); *A61B 1/0005* (2013.01); *A61B 1/00039* (2013.01);
(Continued)

(58) Field of Classification Search
CPC ....... A61B 1/2676; A61B 6/465; A61B 6/466; A61B 6/5223; A61B 34/10;
(Continued)

(56) References Cited

U.S. PATENT DOCUMENTS 4,569,335 A * 2/1986 Tsuno ................ A61B 1/00165
385/117
4,881,810 A * 11/1989 Hasegawa .......... A61B 1/00101
356/241.5

(Continued)

FOREIGN PATENT DOCUMENTS

CN 1658789 A 8/2005
EP 3133995 A2 3/2017

(Continued)

OTHER PUBLICATIONS

Chinese Office Action for application No. 201580042961.1 dated Jan. 29, 2018 with English translation ( 15 pages).

(Continued)

*Primary Examiner* — Timothy J Neal
*Assistant Examiner* — Jae Woo

(57) ABSTRACT

Methods and systems for navigating to a target through a patient's bronchial tree are disclosed including a bronchoscope, a probe insertable into a working channel of the bronchoscope and including a location sensor, and a workstation in operative communication with the probe and the bronchoscope, the workstation including a user interface that guides a user through a navigation plan and is configured to present a central navigation view including a plurality of views configured for assisting the user in navigating the bronchoscope through central airways of the patient's bronchial tree toward the target, a peripheral navigation view including a plurality of views configured for assisting the user in navigating the probe through peripheral airways of the patient's bronchial tree to the target, and a target alignment view including a plurality of views configured for assisting the user in aligning a distal tip of the probe with the target.

19 Claims, 12 Drawing Sheets

Related U.S. Application Data

(60) Provisional application No. 62/020,240, filed on Jul. 2, 2014.

(51) Int. Cl.
  *A61B 1/00* (2006.01)
  *A61B 6/00* (2006.01)
  *A61B 1/267* (2006.01)
  *A61B 34/20* (2016.01)

(52) U.S. Cl.
  CPC .............. *A61B 6/032* (2013.01); *A61B 6/465* (2013.01); *A61B 6/466* (2013.01); *A61B 6/50* (2013.01); *A61B 6/5247* (2013.01); *A61B 1/2676* (2013.01); *A61B 2034/2051* (2016.02)

(58) Field of Classification Search
  CPC ...... A61B 2034/107; A61B 2034/2051; A61L 34/10; A61L 2034/107; A61L 36/2051
  USPC .................................................. 600/117, 118
  See application file for complete search history.

(56) References Cited

U.S. PATENT DOCUMENTS

| | | | |
|---|---|---|---|
| 5,227,985 A * | 7/1993 | DeMenthon | G01S 5/163 345/158 |
| 5,237,647 A * | 8/1993 | Roberts | G06F 3/038 178/18.01 |
| 5,297,061 A * | 3/1994 | Dementhon | G06F 3/0346 345/156 |
| 5,438,975 A * | 8/1995 | Miyagi | A61B 1/00071 600/109 |
| 5,592,939 A | 1/1997 | Martinelli | |
| 5,611,025 A | 3/1997 | Lorensen et al. | |
| 5,676,673 A | 10/1997 | Ferre et al. | |
| 5,697,377 A | 12/1997 | Wittkampf | |
| 5,699,799 A | 12/1997 | Xu et al. | |
| 5,715,836 A | 2/1998 | Kliegis et al. | |
| 5,729,129 A | 3/1998 | Acker | |
| 5,752,513 A | 5/1998 | Acker et al. | |
| 5,782,762 A | 7/1998 | Vining | |
| 5,881,124 A | 3/1999 | Giger et al. | |
| 5,891,030 A | 4/1999 | Johnson et al. | |
| 5,913,820 A | 6/1999 | Bladen et al. | |
| 5,920,319 A | 7/1999 | Vining et al. | |
| 5,967,980 A | 10/1999 | Ferre et al. | |
| 5,971,767 A | 10/1999 | Kaufman et al. | |
| 5,987,960 A | 11/1999 | Messner et al. | |
| 5,995,107 A * | 11/1999 | Berteig | G06T 19/20 345/420 |
| 6,019,725 A | 2/2000 | Vesely et al. | |
| 6,047,080 A | 4/2000 | Chen et al. | |
| 6,083,162 A | 7/2000 | Vining | |
| 6,124,883 A * | 9/2000 | Suzuki | A61B 1/00165 348/68 |
| 6,138,045 A | 10/2000 | Kupinski et al. | |
| 6,151,404 A | 11/2000 | Pieper | |
| 6,167,296 A | 12/2000 | Shahidi | |
| 6,181,348 B1 | 1/2001 | Geiger | |
| 6,201,387 B1 | 3/2001 | Govari | |
| 6,233,476 B1 | 5/2001 | Strommer et al. | |
| 6,246,784 B1 | 6/2001 | Summers et al. | |
| 6,262,734 B1 * | 7/2001 | Ishikawa | G06F 3/04815 345/440 |
| 6,266,551 B1 | 7/2001 | Osadchy et al. | |
| 6,332,089 B1 | 12/2001 | Acker et al. | |
| 6,346,938 B1 * | 2/2002 | Chan | G06F 3/04815 345/419 |
| 6,346,940 B1 | 2/2002 | Fukunaga | |
| 6,352,509 B1 * | 3/2002 | Kawagishi | A61B 8/06 128/916 |
| 6,366,800 B1 | 4/2002 | Vining et al. | |
| 6,381,485 B1 | 4/2002 | Hunter et al. | |
| 6,387,092 B1 | 5/2002 | Burnside et al. | |
| 6,466,815 B1 | 10/2002 | Saito et al. | |
| 6,496,188 B1 | 12/2002 | Deschamps et al. | |
| 6,501,848 B1 | 12/2002 | Carroll et al. | |
| 6,501,981 B1 | 12/2002 | Schweikard et al. | |
| 6,505,065 B1 | 1/2003 | Yanof et al. | |
| 6,522,907 B1 | 2/2003 | Bladen et al. | |
| 6,526,162 B2 | 2/2003 | Asano et al. | |
| 6,535,756 B1 | 3/2003 | Simon et al. | |
| 6,578,579 B2 | 6/2003 | Burnside et al. | |
| 6,584,174 B2 | 6/2003 | Schubert et al. | |
| 6,603,868 B1 | 8/2003 | Ludwig et al. | |
| 6,611,793 B1 | 8/2003 | Burnside et al. | |
| 6,650,927 B1 | 11/2003 | Keidar | |
| 6,651,669 B1 | 11/2003 | Burnside | |
| 6,694,163 B1 | 2/2004 | Vining | |
| 6,757,557 B1 | 6/2004 | Bladen et al. | |
| 6,783,523 B2 | 8/2004 | Qin et al. | |
| 6,792,390 B1 | 9/2004 | Burnside et al. | |
| 6,829,379 B1 | 12/2004 | Knoplioch et al. | |
| 6,850,794 B2 | 2/2005 | Shahidi | |
| 6,892,090 B2 | 5/2005 | Verard et al. | |
| 6,898,263 B2 | 5/2005 | Avinash et al. | |
| 6,909,913 B2 | 6/2005 | Vining | |
| 6,920,347 B2 | 7/2005 | Simon et al. | |
| 6,925,200 B2 | 8/2005 | Wood et al. | |
| 7,006,677 B2 | 2/2006 | Manjeshwar et al. | |
| 7,072,501 B2 | 7/2006 | Wood et al. | |
| 7,085,400 B1 | 8/2006 | Holsing et al. | |
| 7,096,148 B2 | 8/2006 | Anderson et al. | |
| 7,149,564 B2 | 12/2006 | Vining et al. | |
| 7,167,180 B1 | 1/2007 | Shibolet | |
| 7,174,202 B2 | 2/2007 | Bladen et al. | |
| 7,179,220 B2 | 2/2007 | Kukuk | |
| 7,233,820 B2 | 6/2007 | Gilboa | |
| 7,236,558 B2 | 6/2007 | Saito et al. | |
| 7,301,332 B2 | 11/2007 | Govari et al. | |
| 7,315,639 B2 | 1/2008 | Kuhnigk | |
| 7,324,104 B1 | 1/2008 | Bitter et al. | |
| 7,336,809 B2 | 2/2008 | Zeng et al. | |
| 7,397,937 B2 | 7/2008 | Schneider et al. | |
| 7,428,334 B2 | 9/2008 | Schoisswohl et al. | |
| 7,452,357 B2 | 11/2008 | Vlegele et al. | |
| 7,505,809 B2 | 3/2009 | Strommer et al. | |
| 7,517,320 B2 | 4/2009 | Wibowo et al. | |
| 7,518,619 B2 | 4/2009 | Stoval, III et al. | |
| 7,630,752 B2 | 12/2009 | Viswanathan | |
| 7,630,753 B2 | 12/2009 | Simon et al. | |
| 7,659,912 B2 | 2/2010 | Akimoto et al. | |
| 7,702,153 B2 | 4/2010 | Hong et al. | |
| 7,751,865 B2 | 7/2010 | Jascob et al. | |
| 7,756,316 B2 | 7/2010 | Odry et al. | |
| 7,788,060 B2 | 8/2010 | Schneider | |
| 7,792,565 B2 | 9/2010 | Vining | |
| 7,805,269 B2 | 9/2010 | Glossop | |
| 7,809,176 B2 | 10/2010 | Gundel | |
| 7,811,294 B2 | 10/2010 | Strommer et al. | |
| 7,822,461 B2 * | 10/2010 | Geiger | G06T 19/003 600/109 |
| 7,901,348 B2 | 3/2011 | Soper et al. | |
| 7,907,772 B2 | 3/2011 | Wang et al. | |
| 7,929,014 B2 | 4/2011 | Akimoto et al. | |
| 7,951,070 B2 | 5/2011 | Ozaki et al. | |
| 7,969,142 B2 | 6/2011 | Krueger et al. | |
| 7,985,187 B2 | 7/2011 | Wibowo et al. | |
| 8,009,891 B2 | 8/2011 | de Vaan | |
| 8,049,777 B2 | 11/2011 | Akimoto et al. | |
| 8,055,323 B2 | 11/2011 | Sawyer | |
| 8,102,416 B2 | 1/2012 | Ito et al. | |
| 8,126,241 B2 | 2/2012 | Zarkh et al. | |
| 8,131,344 B2 | 3/2012 | Strommer et al. | |
| 8,170,328 B2 | 5/2012 | Masumoto et al. | |
| 8,199,981 B2 | 6/2012 | Koptenko et al. | |
| 8,200,314 B2 | 6/2012 | Bladen et al. | |
| 8,202,213 B2 | 6/2012 | Ito et al. | |
| 8,208,708 B2 | 6/2012 | Homan et al. | |
| 8,219,179 B2 | 7/2012 | Ganatra et al. | |
| 8,257,346 B2 | 9/2012 | Qin et al. | |
| 8,267,927 B2 | 9/2012 | Dalal et al. | |

(56) References Cited

U.S. PATENT DOCUMENTS

| | | | |
|---|---|---|---|
| 8,290,228 B2 | 10/2012 | Cohen et al. | |
| 8,298,135 B2 | 10/2012 | Ito et al. | |
| 8,391,952 B2 | 3/2013 | Anderson | |
| 8,417,009 B2 | 4/2013 | Mizuno | |
| 8,494,612 B2 | 7/2013 | Vetter et al. | |
| 8,509,877 B2 | 8/2013 | Mori et al. | |
| 8,585,598 B2 * | 11/2013 | Razzaque | A61B 18/1477 600/439 |
| 8,641,621 B2 * | 2/2014 | Razzaque | A61B 34/20 600/407 |
| 8,672,836 B2 | 3/2014 | Higgins et al. | |
| 8,682,045 B2 | 3/2014 | Vining et al. | |
| 8,696,549 B2 | 4/2014 | Holsing et al. | |
| 8,698,806 B2 | 4/2014 | Kunert et al. | |
| 8,700,132 B2 * | 4/2014 | Ganatra | A61B 34/20 600/424 |
| 8,706,193 B2 | 4/2014 | Govari et al. | |
| 8,709,034 B2 | 4/2014 | Keast et al. | |
| 8,730,237 B2 | 5/2014 | Ruijters et al. | |
| 8,768,029 B2 | 7/2014 | Helm et al. | |
| 8,784,400 B2 | 7/2014 | Roschak | |
| 8,798,227 B2 | 8/2014 | Tsukagoshi et al. | |
| 8,798,339 B2 | 8/2014 | Mielekamp et al. | |
| 8,801,601 B2 | 8/2014 | Prisco et al. | |
| 8,819,591 B2 | 8/2014 | Wang et al. | |
| 8,821,376 B2 * | 9/2014 | Tolkowsky | A61B 1/0052 600/101 |
| 8,862,204 B2 | 10/2014 | Sobe et al. | |
| 9,226,687 B2 * | 1/2016 | Soper | A61B 1/0008 |
| 9,770,216 B2 | 9/2017 | Brown et al. | |
| 2002/0193677 A1 * | 12/2002 | Thornton | A61B 6/12 600/407 |
| 2006/0033728 A1 * | 2/2006 | Sako | A61B 6/463 345/204 |
| 2006/0235671 A1 * | 10/2006 | Kirchberg | G06F 19/321 703/11 |
| 2006/0239400 A1 * | 10/2006 | Sukovic | A61B 6/032 378/38 |
| 2007/0167714 A1 * | 7/2007 | Kiraly | A61B 1/2676 600/407 |
| 2007/0257903 A1 * | 11/2007 | Gutierrez | G06T 17/05 345/419 |
| 2007/0288207 A1 * | 12/2007 | Backe | G06F 17/5004 703/1 |
| 2008/0183073 A1 | 7/2008 | Higgins et al. | |
| 2008/0207997 A1 * | 8/2008 | Higgins | A61B 1/00009 600/114 |
| 2008/0319317 A1 * | 12/2008 | Kamiyama | A61B 8/0825 600/443 |
| 2009/0003668 A1 * | 1/2009 | Matsumoto | A61B 5/055 382/128 |
| 2009/0012390 A1 * | 1/2009 | Pescatore | A61B 6/12 600/425 |
| 2009/0030306 A1 * | 1/2009 | Miyoshi | A61B 1/005 600/424 |
| 2009/0036902 A1 * | 2/2009 | DiMaio | A61B 34/37 606/130 |
| 2009/0099452 A1 * | 4/2009 | Hashimoto | A61B 8/463 600/443 |
| 2010/0004509 A1 * | 1/2010 | Naito | A61B 1/0055 600/141 |
| 2010/0310146 A1 | 12/2010 | Higgins et al. | |
| 2010/0312094 A1 * | 12/2010 | Guttman | A61B 5/415 600/411 |
| 2011/0237897 A1 * | 9/2011 | Gilboa | A61B 1/00154 600/202 |
| 2011/0251607 A1 | 10/2011 | Kruecker et al. | |
| 2012/0059248 A1 * | 3/2012 | Holsing | A61B 1/2676 600/424 |
| 2012/0203065 A1 | 8/2012 | Higgins et al. | |
| 2012/0249546 A1 | 10/2012 | Tschirren et al. | |
| 2012/0259204 A1 * | 10/2012 | Carrat | A61B 5/061 600/414 |
| 2012/0280135 A1 | 11/2012 | Bal | |
| 2012/0287238 A1 | 11/2012 | Onishi et al. | |
| 2013/0165854 A1 * | 6/2013 | Sandhu | A61B 6/12 604/95.01 |
| 2013/0197357 A1 * | 8/2013 | Green | A61B 8/0841 600/424 |
| 2013/0223702 A1 * | 8/2013 | Holsing | A61B 5/113 382/128 |
| 2013/0281838 A1 * | 10/2013 | Trumer | A61B 6/12 600/424 |
| 2014/0051986 A1 * | 2/2014 | Zhao | A61B 5/066 600/424 |
| 2014/0088457 A1 * | 3/2014 | Johnson | A61B 17/12104 600/567 |
| 2014/0187949 A1 * | 7/2014 | Zhao | A61B 8/12 600/443 |
| 2014/0267031 A1 * | 9/2014 | Huebner | G06F 3/0346 345/158 |
| 2014/0276005 A1 * | 9/2014 | Forsyth | A61B 5/0071 600/424 |
| 2014/0276033 A1 * | 9/2014 | Brannan | A61B 6/03 600/431 |
| 2014/0282216 A1 * | 9/2014 | Baker | G16H 40/63 715/781 |
| 2014/0359535 A1 * | 12/2014 | Little | G06F 3/04886 715/848 |
| 2015/0305650 A1 * | 10/2015 | Hunter | A61B 1/0005 600/424 |

FOREIGN PATENT DOCUMENTS

| | | |
|---|---|---|
| JP | 2002119507 A | 4/2002 |
| JP | 2004097696 A | 4/2004 |
| WO | 03086498 A2 | 10/2003 |
| WO | 2011102012 A1 | 8/2011 |
| WO | 2013080131 A1 | 6/2013 |
| WO | 2015164587 A2 | 10/2015 |

OTHER PUBLICATIONS

Chinese Third Office Action for application No. 201580042961.1 dated Feb. 12, 2019, together with English ranslation (10 pages).
Japanese Office Action issued in corresponding Appl. No. JP 2016-575062, dated Mar. 1, 2019, together with English language translation (10 pages).
International Search Report, dated Sep. 18, 2015, for corresponding International Application No. PCT/US2015/038478.
Extended European Search Report for application No. 15814496.4 dated Feb. 14, 2018 (10 pages).
Luo, et al., Beyond Current Guided Bronchoscopy: A Robust and Real-time Bronchoscopic Ultrasound Navigation System, MICCAI 2013, Part 1, LNCS 8149, pp. 388-395, 2013.
Australian Examination Report No. 2 issued in corresponding Appl. No. AU 2015284283 dated Feb. 22, 2019 (3 pages).
Chinese Second Office Action for application No. 201580042961.1 dated Aug. 10, 2018 with English translation (9 pages).
European Examination Report issued in corresponding Appl. No. EP 15814496.4 dated Aug. 27, 2019 (5 pages).
superDimensionENB: "The SuperDimension In Reach(TM) SystemsuperDimension's ilogic Promotional Video", Jun. 8, 2010 (Jun. 8, 2010), p. 1, XP054979599, Retrieved from the Internet: URL:https://www.youtube.com/watch?v=3oCkvD8eaMQ [retrieved on Aug. 15, 2019].
Australian Examination Report No. 1 issued in corresponding Appl. No. AU 2019204524 dated Sep. 9, 2019 (3 pages).
Rejection Decision issued in corresponding Chinese Appl. No. CN 201580042961.1 dated Jun. 27, 2019, together with English language translation (8 pages).
Japanese Notice of Allowance issued in corresponding Appl. No. JP 2016-575062 dated May 22, 2020 (3 pages) together with English language translation (2 pages).

* cited by examiner

SYSTEM AND METHOD FOR NAVIGATING WITHIN THE LUNG

CROSS REFERENCE TO RELATED APPLICATIONS

The present application claims the benefit of and priority to U.S. Provisional Patent Application Ser. No. 62/020,240 filed on Jul. 2, 2014, the entire contents of which are incorporated herein by reference.

BACKGROUND

Technical Field

The present disclosure relates to devices, systems, and methods for navigating within the lung.

Description of Related Art

A common device for inspecting the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

Bronchoscopes, however, are limited in how far they may be advanced through the airways due to their size. Where the bronchoscope is too large to reach a target location deep in the lungs a clinician may utilize certain real-time imaging modalities such as fluoroscopy. Fluoroscopic images, while useful present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these issues systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™) system currently sold by Covidien LP. The details of such a system are described in the commonly assigned U.S. Pat. No. 7,233,820, filed on Mar. 29, 2004 by Gilboa and entitled ENDOSCOPE STRUCTURES AND TECHNIQUES FOR NAVIGATING TO A TARGET IN BRANCHED STRUCTURE, the contents of which are incorporated herein by reference.

While the system as described in U.S. Pat. No. 7,233,820 is quite capable, there is always a need for development of improvements and additions to such systems.

SUMMARY

Provided in accordance with the present disclosure is a system for navigating to a target through a patient's bronchial tree.

In an aspect of the present disclosure, the system includes a bronchoscope configured for insertion into the patient's bronchial tree, a probe insertable into a working channel of the bronchoscope, and a workstation in operative communication with the probe and the bronchoscope. The probe includes a location sensor and is configured to navigate through the patient's bronchial tree. The workstation includes a memory and at least one processor. The memory stores a navigation plan and a program that, when executed by the processor, presents a user interface that guides a user through the navigation plan. The user interface is configured to present a central navigation view including a plurality of views configured for assisting the user in navigating the bronchoscope through central airways of the patient's bronchial tree toward the target, a peripheral navigation view including a plurality of views configured for assisting the user in navigating the probe through peripheral airways of the patient's bronchial tree to the target, and a target alignment view including a plurality of views configured for assisting the user in aligning a distal tip of the probe with the target.

In a further aspect of the present disclosure, each of the central navigation view, peripheral navigation view, and target alignment view are configured to present one or more views selected from the group consisting of a bronchoscope view, a virtual bronchoscope view, a local view, a MIP view, a 3D map dynamic view, a 3D map static view, a sagittal CT view, an axial CT view, a coronal CT view, a tip view, a 3D CT view, and an alignment view.

In another aspect of the present disclosure, the central navigation view is configured to present the bronchoscope view, virtual bronchoscope view, and 3D map dynamic view.

In yet another aspect of the present disclosure, the peripheral navigation view is configured to present the bronchoscope view, 3D map dynamic view, tip view, and local view.

In an aspect of the present disclosure, the target alignment view is configured to present the 3D map dynamic view, local view, alignment view, and 3D CT view.

In another aspect of the present disclosure, the 3D map dynamic view includes a 3D model of the patient's bronchial tree. The 3D map dynamic view may be configured to automatically adjust the orientation of the 3D model in response to movement of the location sensor within the patient's airways.

In a further aspect of the present disclosure, the 3D model includes a highlighted portion indicating a pathway along the patient's bronchial tree to the target.

In another aspect of the present disclosure, at least one of the 3D map dynamic view or the local view includes a virtual representation of the distal tip of the probe. The virtual representation may be configured to provide the user with an indication of an orientation of the distal tip of the probe.

In a further aspect of the present disclosure, the virtual representation of the distal tip of the probe is a 3D virtual representation.

In yet a further aspect of the present disclosure, the distal tip of the probe defines a configuration selected from the group consisting of a linear, a curved, or an angled configuration. The virtual representation of the distal tip of the probe may have the same configuration as the distal tip of the probe.

In another aspect of the present disclosure, the 3D map dynamic view and/or the local view is configured to adjust the orientation of the virtual representation of the distal tip of the probe in response to a change in orientation of the distal tip of the probe within the patient's airways.

In a further aspect of the present disclosure, the virtual bronchoscope view includes a virtual pathway configured to provide the user with an indication of a pathway leading toward the target.

In yet another aspect of the present disclosure, the local view presents an elevated view of a slice of a 3D volume of the navigation plan. The local view may be configured to change the slice of the 3D volume to be presented in response to movement of the probe within the patient's bronchial tree.

In a further aspect of the present disclosure, the local view includes a 3D representation of the target disposed relative to the presented slice of the 3D volume. The presented slice of the 3D volume may define a watermark against the 3D representation of the target indicating a relative position of the 3D representation of the target to the presented slice of the 3D volume.

In yet another aspect of the present disclosure, a first portion of the 3D representation of the target disposed above the presented slice of the 3D volume is presented as a first color, and a second portion of the 3D representation of the target disposed below the presented slice of the 3D volume is presented as a second color.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

Figure 1:
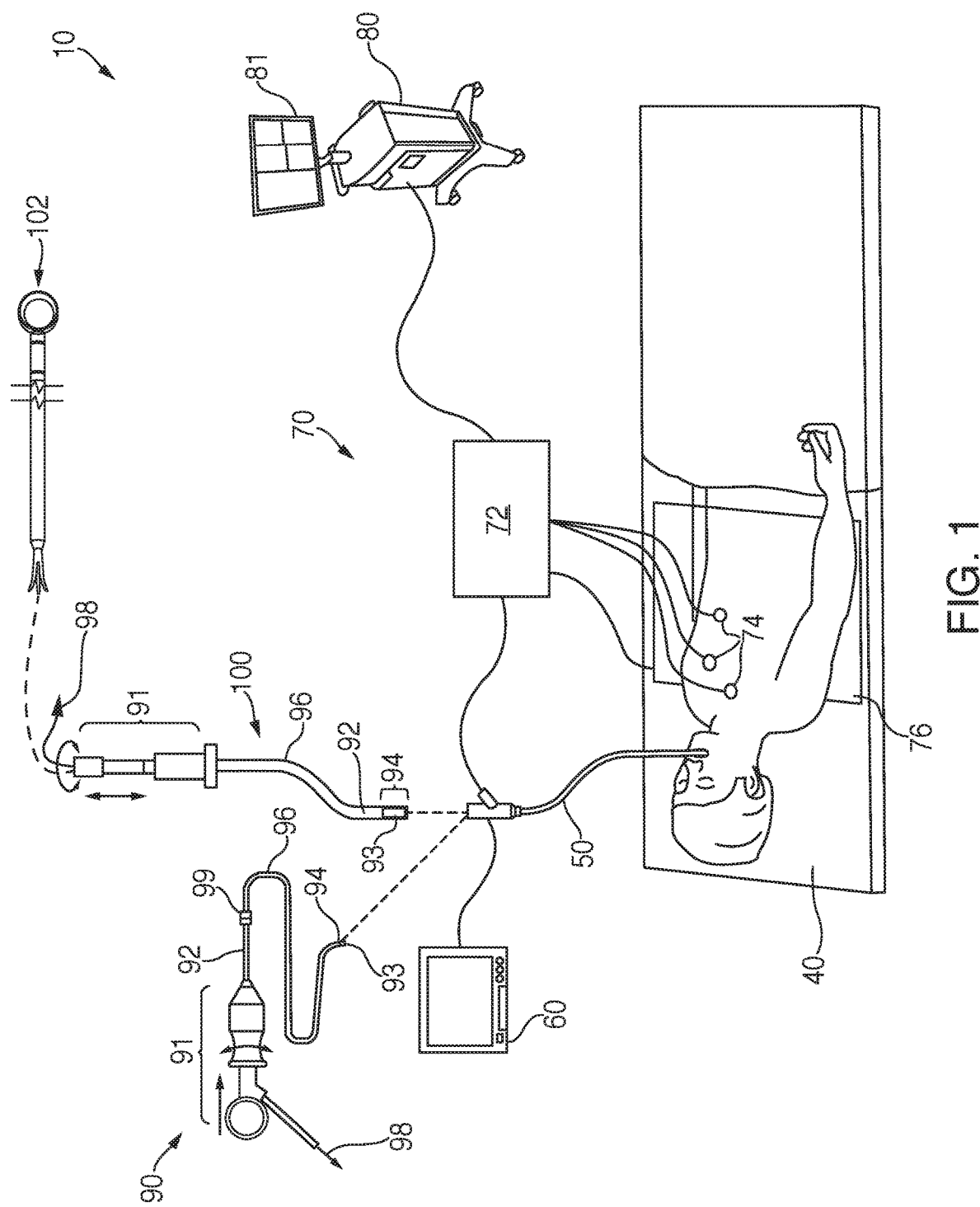
FIG. 1 is a perspective view of an electromagnetic navigation system in accordance with the present disclosure.

Devices, systems, and methods for navigating to a target within a luminal network, for example, a patient's lungs, are provided in accordance with the present disclosure and described in detail below. The disclosed navigation system and method provides a clinician with an easy to use workflow guiding the clinician through the various steps involved in performing navigation to a target in the luminal network. For example, the disclosed navigation system and method walk a clinician through a procedure which includes loading a navigation plan, performing registration, performing central navigation with a bronchoscope, performing peripheral navigation with an extended working channel and locatable guide, performing target alignment, performing a virtual biopsy or treatment location marking, and finally performing a biopsy or treatment of the target. The navigation plan may be based on a three-dimensional model of a patient's lungs. Various methods for generating the 3D model are envisioned, some of which are more fully described in co-pending U.S. patent application Ser. Nos. 13/838,805, 13/838,997, and 13/839,224, all entitled PATHWAY PLANNING SYSTEM AND METHOD, filed on Mar. 15, 2013, by Baker, the entire contents of all of which are incorporated herein by reference. The disclosed navigation system and method also provide the clinician with the capability to virtually mark and track the locations of multiple biopsies or treatments and to easily return to the marked biopsy or treatment locations.

Additional features of the ENB system of the present disclosure are described in co-pending U.S. Provisional Patent Application Nos. 62/020,238, entitled INTELLIGENT DISPLAY, filed on Jul. 2, 2014, by KEHAT et al.; 62/020,242, entitled UNIFIED COORDINATE SYSTEM FOR MULTIPLE CT SCANS OF PATIENT LUNGS, filed on Jul. 2, 2014, by Greenburg; 62/020,245, entitled ALIGNMENT CT, filed on Jul. 2, 2014, by Klein et al.; 62/020,250, entitled ALGORITHM FOR FLUOROSCOPIC POSE ESTIMATION, filed on Jul. 2, 2014, by Merlet; 62/020,253, entitled TRACHEA MARKING, filed on Jul. 2, 2014, by Lachmanovich et al.; 62/020,257, entitled AUTOMATIC DETECTION OF HUMAN LUNG TRACHEA, filed on Jul. 2, 2014, by Markov et al.; 62/020,261, entitled LUNG AND PLEURA SEGMENTATION, filed on Jul. 2, 2014, by Markov et al.; 62/020,258, entitled CONE VIEW—A METHOD OF PROVIDING DISTANCE AND ORIENTATION FEEDBACK WHILE NAVIGATING IN 3D, filed on Jul. 2, 2014, by Lachmanovich et al.; and 62/020,262, entitled DYNAMIC 3D LUNG MAP VIEW FOR TOOL NAVIGATION INSIDE THE LUNG, filed on Jul. 2, 2014, by Weingarten et al., the entire contents of all of which are incorporated herein by reference.

However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the following embodiments are described in terms of bronchoscopy of a patient's airways, those skilled in the art will recognize that the same or similar devices, systems, and methods may be used in other luminal networks, such as, for example, the vascular, lymphatic, and/or gastrointestinal networks as well.

With reference to FIG. 1, an electromagnetic navigation (EMN) system 10 is provided in accordance with the present disclosure. One such ENM system is the ELECTROMAGNETIC NAVIGATION BRONCHOSCOPY® system currently sold by Covidien LP. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool, digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the biopsy location.

FIG. 1 also depicts two types of catheter guide assemblies 90, 100. Both catheter guide assemblies 90, 100 are usable with the EMN system 10 and share a number of common components. Each catheter guide assembly 90, 100 includes a handle 91, which is connected to an extended working channel (EWC) 96. The EWC 96 is sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip 93 of the EWC 96. The location of the EM sensor 94, and thus the distal end of the EWC 96, within an electromagnetic field generated by the electromagnetic field generator 76, can be derived by the tracking module 72 and the workstation 80. Catheter guide assemblies 90, 100 have different operating mechanisms, but each contain a handle 91 that can be manipulated by rotation and compression to steer the distal tip 93 of the LG 92, extended working channel 96. Catheter guide assemblies 90 are currently marketed and sold by Covidien LP under the name SUPER-DIMENSION® Procedure Kits. Similarly, catheter guide assemblies 100 are currently sold by Covidien LP under the name EDGE™ Procedure Kits. Both kits include a handle 91, extended working channel 96, and locatable guide 92. For a more detailed description of the catheter guide assemblies 90, 100, reference is made to commonly-owned U.S. patent application Ser. No. 13/836,203 filed on Mar. 15, 2013 by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). The LG 92 and EWC 96 are selectively lockable relative to one another via a locking mechanism 99. A six degrees-of-freedom electromagnetic tracking system 70, e.g., those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of the EM sensor 94 as it moves in conjunction with the EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes application 81 where sensors 74 are used to calculate a patient coordinate frame of reference.

Also shown in FIG. 1 is a catheter biopsy tool 102 that is insertable into the catheter guide assemblies 90,100 following navigation to a target and removal of the LG 92. The biopsy tool 102 is used to collect one or more tissue sample from the target tissue. As detailed below, biopsy tool 102 is further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained.

Although navigation is detailed above with respect to EM sensor 94 being included in the LG 92 it is also envisioned that EM sensor 94 may be embedded or incorporated within biopsy tool 102 where biopsy tool 102 may alternatively be utilized for navigation without need of the LG or the necessary tool exchanges that use of the LG requires. A variety of useable biopsy tools are described in U.S. Provisional Patent Application Nos. 61/906,732 and 61/906,762, both entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013 and U.S. Provisional Patent Application No. 61/955,407 having the same title and filed Mar. 14, 2014, the entire contents of each of which are incorporated herein by reference and useable with the EMN system 10 as described herein.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 81 associated with workstation 80 or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. patent application Ser. Nos. 13/838,805; 13/838,997; and 13/839,224, filed on Mar. 15, 2014, the entire contents of each of which are incorporated herein by reference.

During navigation, EM sensor 94, in conjunction with tracking system 70, enables tracking of EM sensor 94 and/or biopsy tool 102 as EM sensor 94 or biopsy tool 102 is advanced through the patient's airways.

Figure 2:
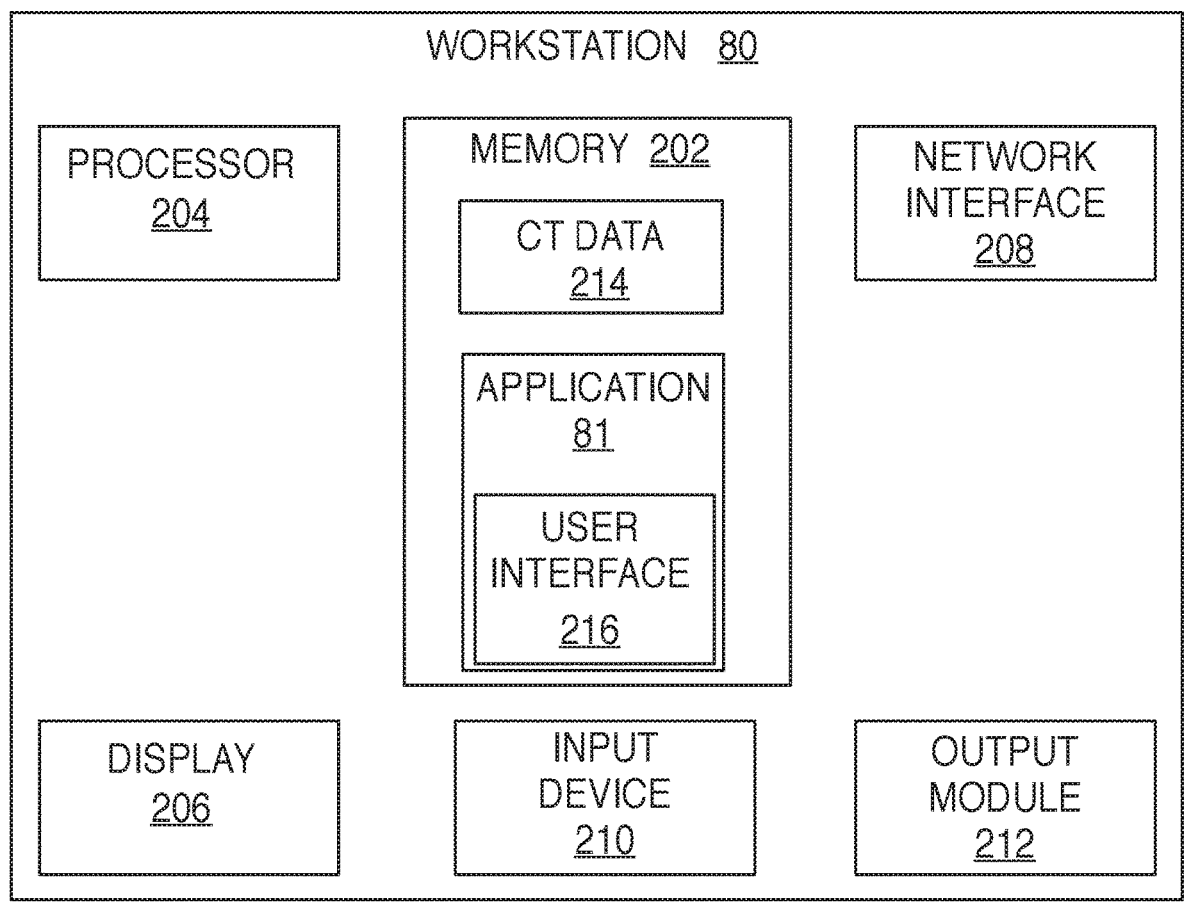
FIG. 2 is a schematic diagram of a workstation configured for use with the system of FIG. 1.

Turning now to FIG. 2, there is shown a system diagram of workstation 80. Workstation 80 may include memory 202, processor 204, display 206, network interface 208, input device 210, and/or output module 212.

Memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3:
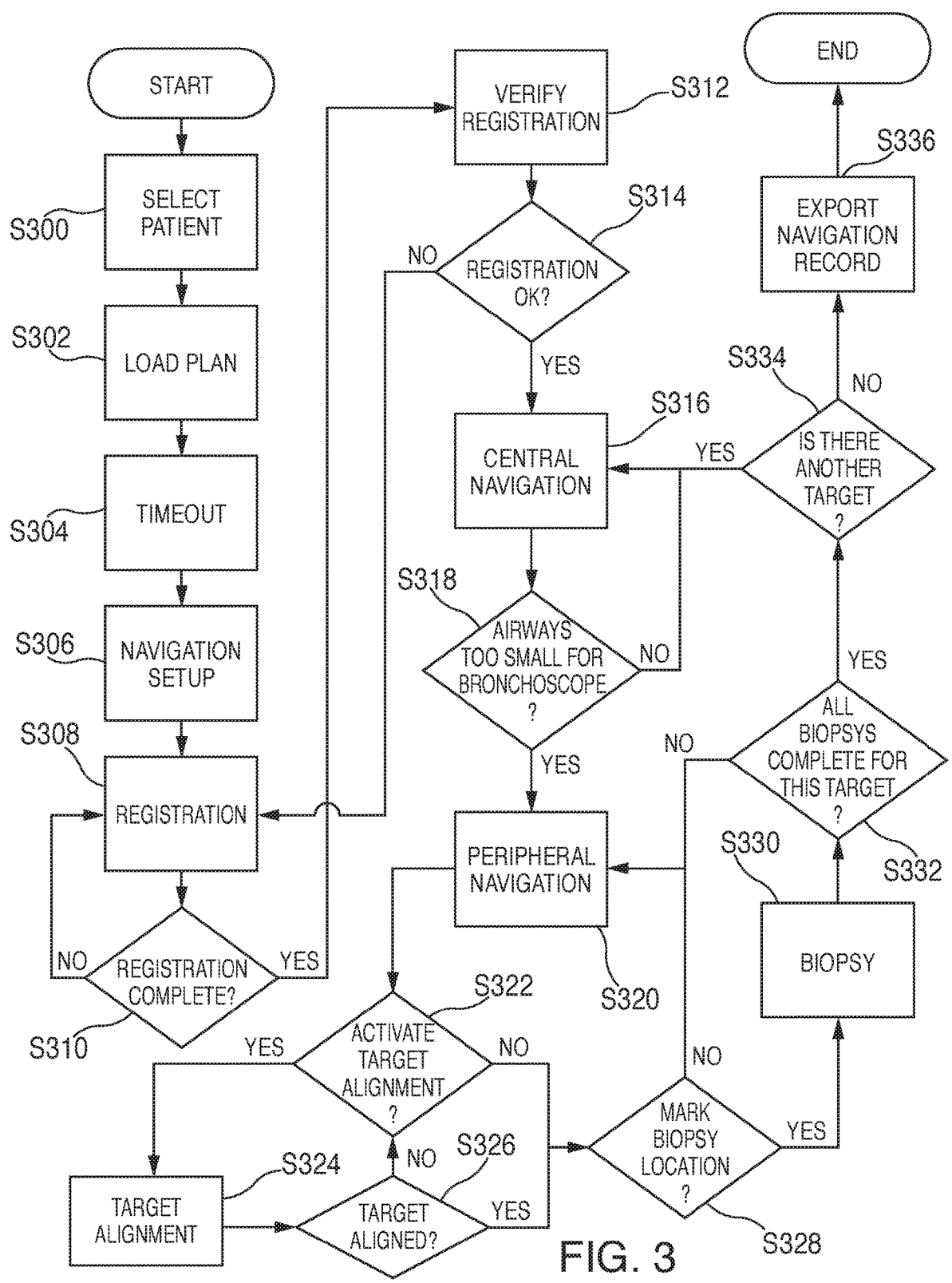
FIG. 3 is a flow chart illustrating a method of navigation in accordance with an embodiment of the present disclosure.

FIG. 3 depicts an exemplary method of navigation using the navigation workstation 80 and the user interface 216. In step S300, user interface 216 presents the clinician with a view (not shown) for the selection of a patient. The clinician may enter patient information such as, for example, the patient name or patient ID number, into a text box to select a patient on which to perform a navigation procedure. Alternatively, the patient may be selected from a drop down menu or other similar methods of patient selection. Once the patient has been selected, the user interface 216 presents clinician with a view (not shown) including a list of available navigation plans for the selected patient. In step S302, the clinician may load one of the navigation plans by activating the navigation plan. The navigation plans may be imported from a procedure planning software.

Once the patient has been selected and a corresponding navigation plan has been loaded, the user interface 216 presents the clinician with a patient details view (not shown) in step S304 which allows the clinician to review the selected patient and plan details. Examples of patient details presented to the clinician in the timeout view may include the patient's name, patient ID number, and birth date. Examples of plan details include navigation plan details, automatic registration status, and/or manual registration status. For example, the clinician may activate the navigation plan details to review the navigation plan, and may verify the availability of automatic registration and/or manual registration. The clinician may also activate an edit button (not shown) to edit the loaded navigation plan from the patient details view. Activating the edit button (not shown) of the loaded navigation plan may also activate the planning software described above. Once the clinician is satisfied that the patient and plan details are correct, the clinician proceeds to navigation setup in step S306. Alternatively, medical staff may perform the navigation setup prior to or concurrently with the clinician selecting the patient and navigation plan.

During navigation setup in step S306, the clinician or other medical staff prepares the patient and operating table by positioning the patient on the operating table over the electromagnetic field generator 76. The clinician or other medical staff position reference sensors 74 on the patient's chest and verify that the sensors are properly positioned, for example, through the use of a setup view (not shown) presented to the clinician or other medical staff by user interface 216. Setup view may, for example, provide the clinician or other medical staff with an indication of where the reference sensors 74 are located relative to the magnetic field generated by the transmitter mat 76. Patient sensors allow the navigation system to compensate for patient breathing cycles during navigation. The clinician also prepares LG 92, EWC 96, and bronchoscope 50 for the procedure by inserting LG 92 into EWC 96 and inserting both LG 92 and EWC 96 into the working channel of bronchoscope 50 such that distal tip 93 of LG 92 extends from the distal end of the working channel of bronchoscope 50. For example, the clinician may extend the distal tip 93 of LG 92 10 mm beyond the distal end of the working channel of bronchoscope 50.

Figure 4:
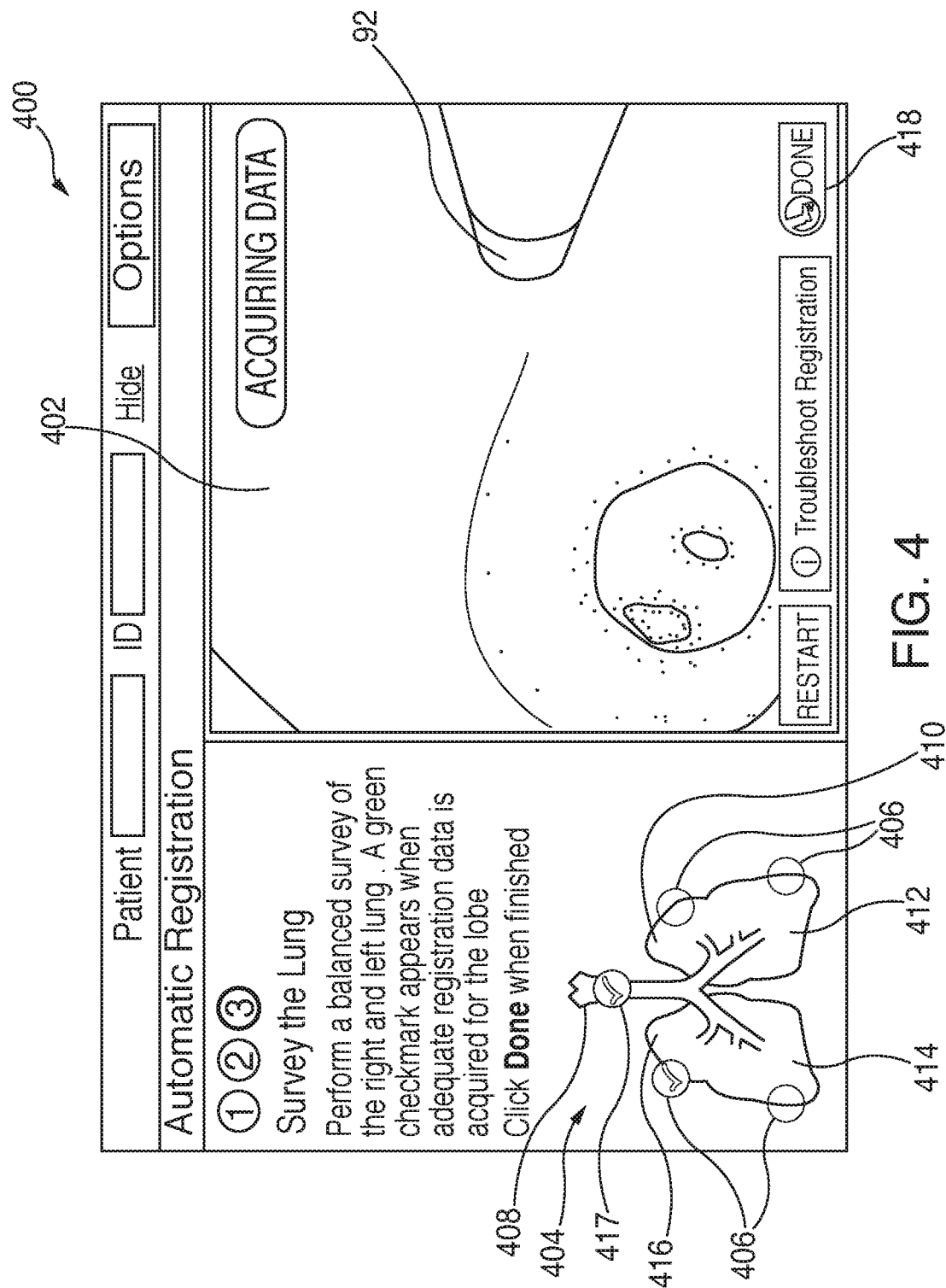
FIG. 4 is an illustration of a user interface of the workstation of FIG. 2 presenting a view for performing registration in accordance with the present disclosure.

Once setup is complete, the user interface 216 presents the clinician with a view 400 for registering the location of LG 92 relative to the loaded navigation plan. In step S308 the clinician prepares for registration by inserting bronchoscope 50 with EWC 96, LG 92 and EM sensor 94 into the patient's airway until the distal ends of the LG 92, the EM sensor 94, and bronchoscope 50 are positioned within the patient's trachea, for example, as shown in FIG. 4. The clinician then activates registration via input device 210, for example, a mouse or foot pedal. As shown in FIG. 4, view 400 presents a clinician with a video feed 402 from bronchoscope 50 and a lung survey 404. Video feed 402 from bronchoscope 50 provides the clinician with a real-time video of the interior of the patient's airways at the distal end of bronchoscope 50. Video feed 402 allows the clinician to visually navigate through the airways of the lungs.

Lung survey 404 provides the clinician with indicators 406 for the trachea 408 and each region 410, 412, 414, and 416 of the lungs. Regions 410, 412, 414, may also correspond to the patient's lung lobes. It is contemplated that an additional region (not shown) may be present and may correspond to the fifth lung lobe, e.g. the middle lung lobe in the patient's right lung. Lung survey 404 may also be modified for patients in which all or a part of one of the lungs is missing, for example, due to prior surgery.

During registration, the clinician advances bronchoscope 50 and LG 92 into each region 410, 412, 414, and 416 until the corresponding indicator 406 is activated. For example, the corresponding indicator may display a "check mark" symbol 417 when activated. As described above, the location of the EM sensor 94 at the distal tip 93 of LG 92 relative to each region 410, 412, 414, and 416 is tracked by the electromagnetic interaction between EM sensor 94 of LG 92 and the electromagnetic field generator 76 and may activate an indicator 406 when the EM sensor 94 enters a corresponding region 410, 412, 414, or 416.

Figure 5:
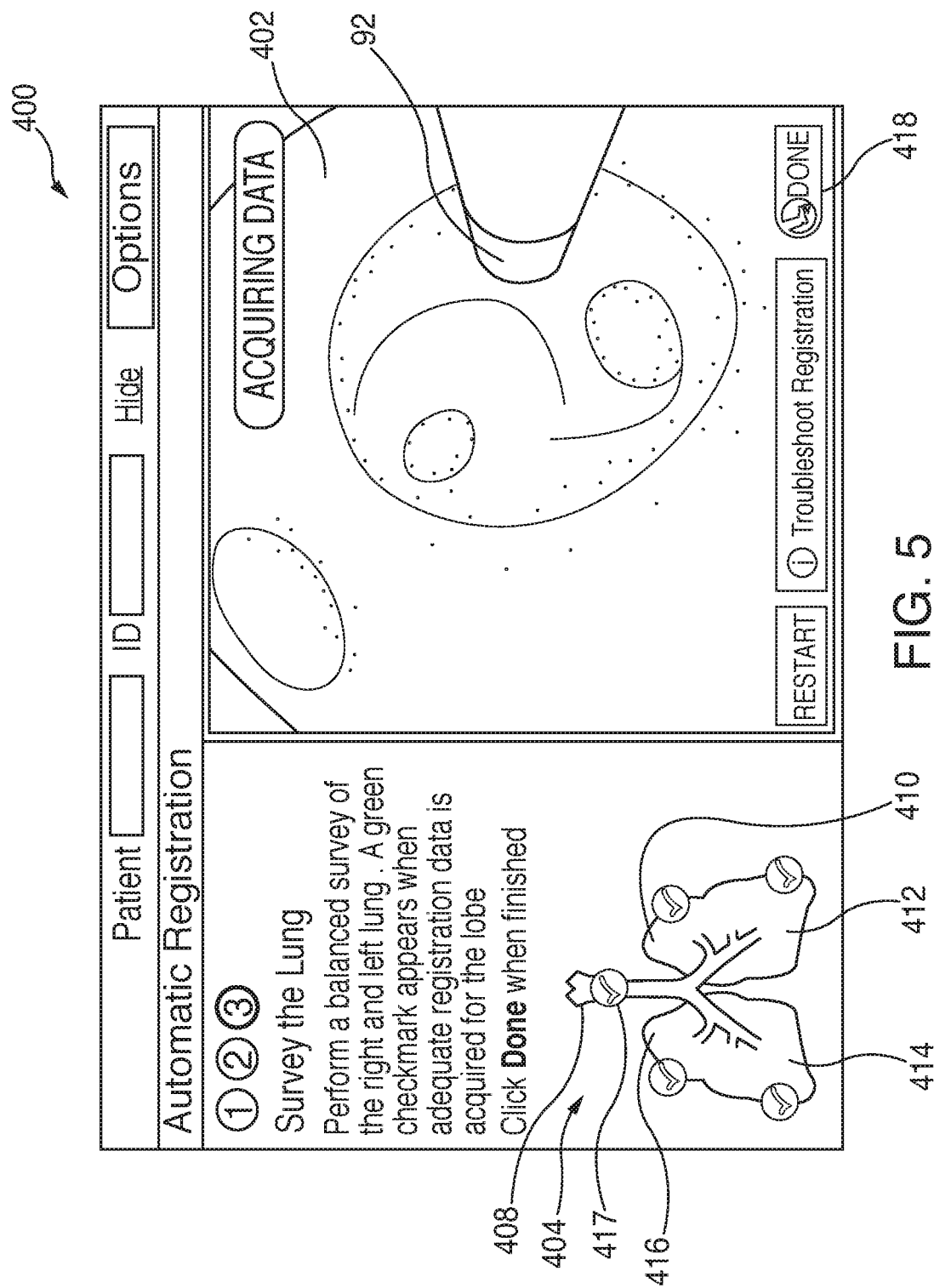
FIG. 5 is an illustration of the view of FIG. 4 with each indicator activated.

In step S310, once the indicators 406 for the trachea 408 and each region 410, 412, 414, and 416 have been activated, for example, as shown in FIG. 5, the clinician activates the "done" button 418 via input device 210, for example, a mouse or foot pedal, and proceeds to verification of the registration in step S312. Although each indicator 406 is shown as activated in FIG. 5, the clinician may alternatively achieve registration with the currently loaded navigation plan while one or more of regions 410, 412, 414, and 416 are not activated. For example, so long as the clinician has achieved sufficient registration with the currently loaded navigation plan the clinician may activate the "done" button 418 to proceed to registration verification in step S312. More details regarding the process of registration are set forth in U.S. Provisional Patent Application No. 62/020,220, entitled REAL-TIME AUTOMATIC REGISTRATION FEEDBACK, filed on Jul. 2, 2014, by Brown et al., the entire contents of which is incorporated herein by reference. Sufficient registration may depend on both the patient's lung structure and the currently loaded navigation plan where, for example, only the indicators 406 for the trachea 408 and one or more of the regions 410, 412, 414, or 416 in one of the lungs may be necessary to achieve a useable registration where the plan identifies targets in one lung.

Figure 6:
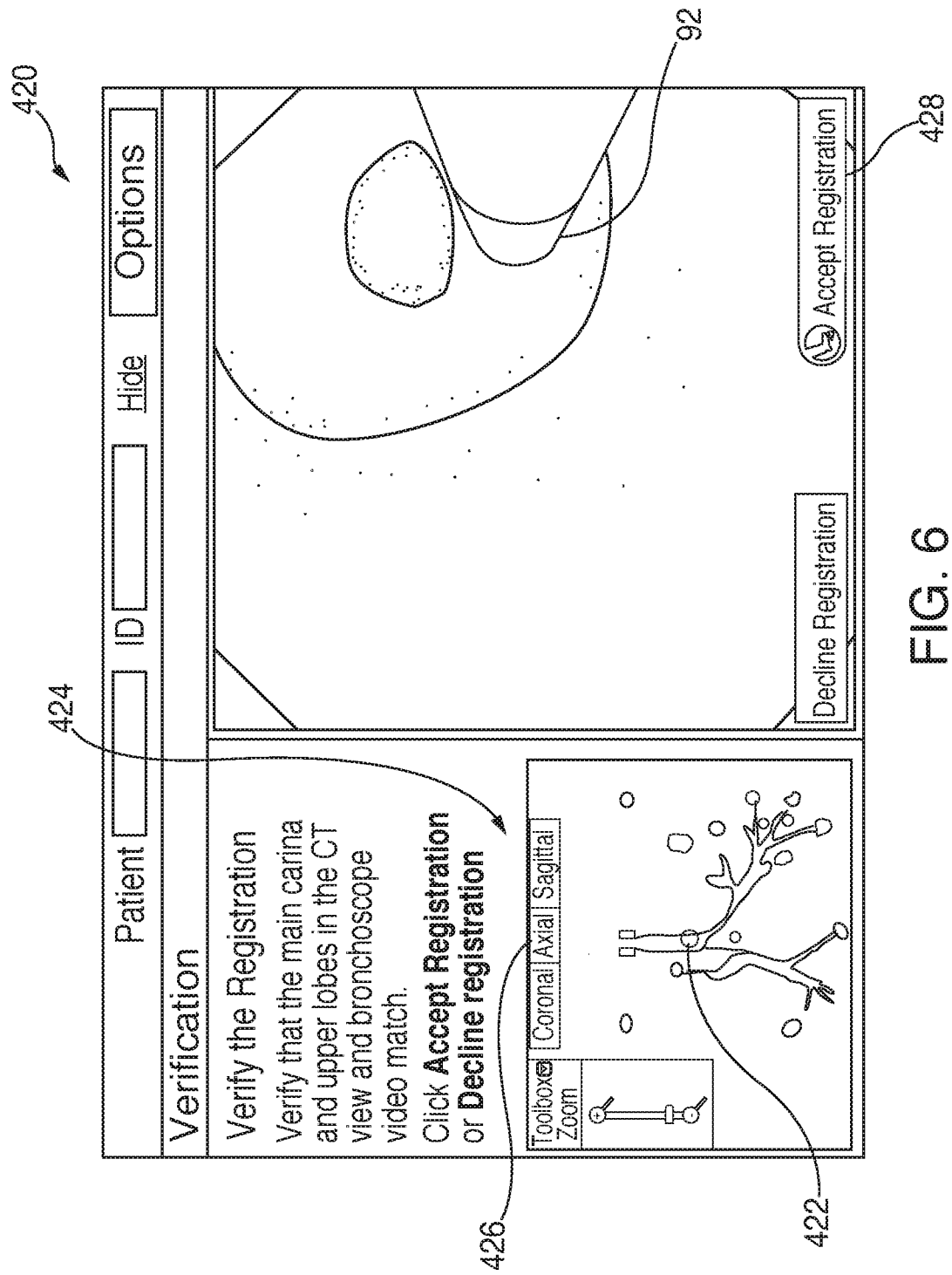
FIG. 6 is an illustration of a user interface of the workstation of FIG. 2, presenting a view for verifying registration in accordance with the present disclosure.

After registration with the currently loaded navigation plan is complete, user interface 216 presents the clinician with a view 420 for registration verification in step S312. View 420 presents the clinician with an LG indicator 422 (actually depicting the location of the EM sensor 94) overlaid on a displayed slice 424 of the 3D volume of the currently loaded navigation plan, for example, as shown in FIG. 6. Although the slice 424 displayed in FIG. 6 is from the coronal direction, the clinician may alternatively select one of the axial or sagittal directions by activating a display bar 426. As the clinician advances the LG 92 and bronchoscope 50 through the patient's airways, the displayed slice 424 changes based on the position of the EM sensor 94 of LG 92 relative to the registered 3D volume of the navigation plan. The clinician then determines whether the registration is acceptable in step S314. Once the clinician is satisfied that the registration is acceptable, for example, that the LG indicator 422 does not stray from within the patient's airways as presented in the displayed slice 424, the clinician accepts the registration by activating the "accept registration" button 428 and proceeds to navigation in step S316. Although registration has now been completed by the clinician, the EMN system 10 may continue to track the location of the EM sensor 94 of LG 92 within the patient's airways relative to the 3D volume and may continue to update and improve the registration during the navigation procedure.

Figure 7:
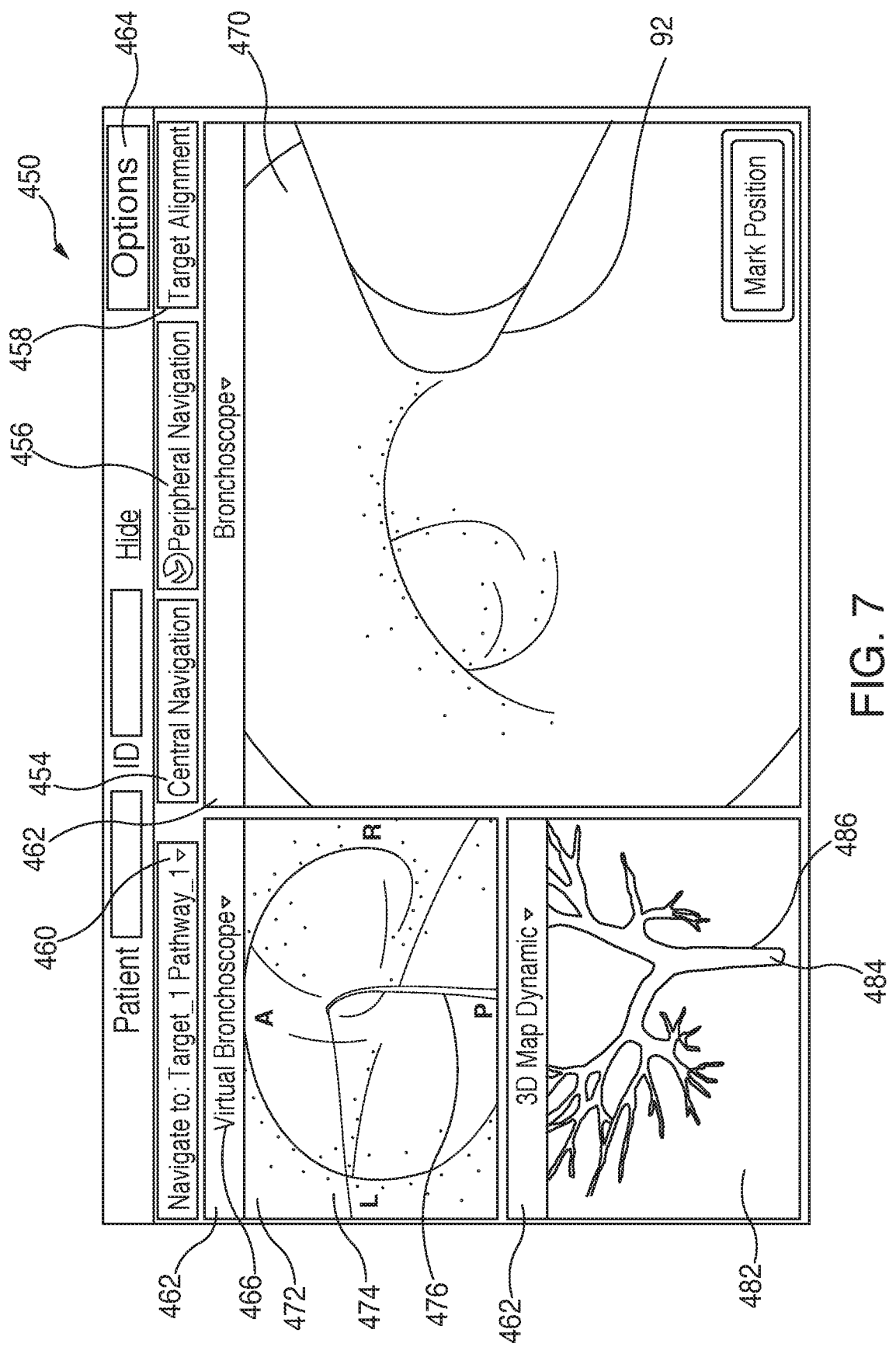
FIG. 7 is an illustration of a user interface of the workstation of FIG. 2 presenting a view for performing navigation to a target further presenting a central navigation tab.

During navigation, user interface 216 presents the clinician with a view 450, as shown, for example, in FIG. 7. View 450 provides the clinician with a user interface for navigating to a target 452 (FIG. 8) including a central navigation tab 454, a peripheral navigation tab 456, and a target alignment tab 458. Central navigation tab 454 is primarily used to guide the bronchoscope 50 through the patient's bronchial tree until the airways become small enough that the bronchoscope 50 becomes wedged in place and is unable to advance. Peripheral navigation tab 456 is primarily used to guide the EWC 96, EM sensor 94, and LG 92 toward target 452 (FIG. 8) after the bronchoscope 50 is wedged in place. Target alignment tab 458 is primarily used to verify that LG 92 is aligned with the target 452 after LG 92 has been navigated to the target 452 using the peripheral navigation tab 456. View 450 also allows the clinician to select target 452 to navigate by activating a target selection button 460.

Figure 10:
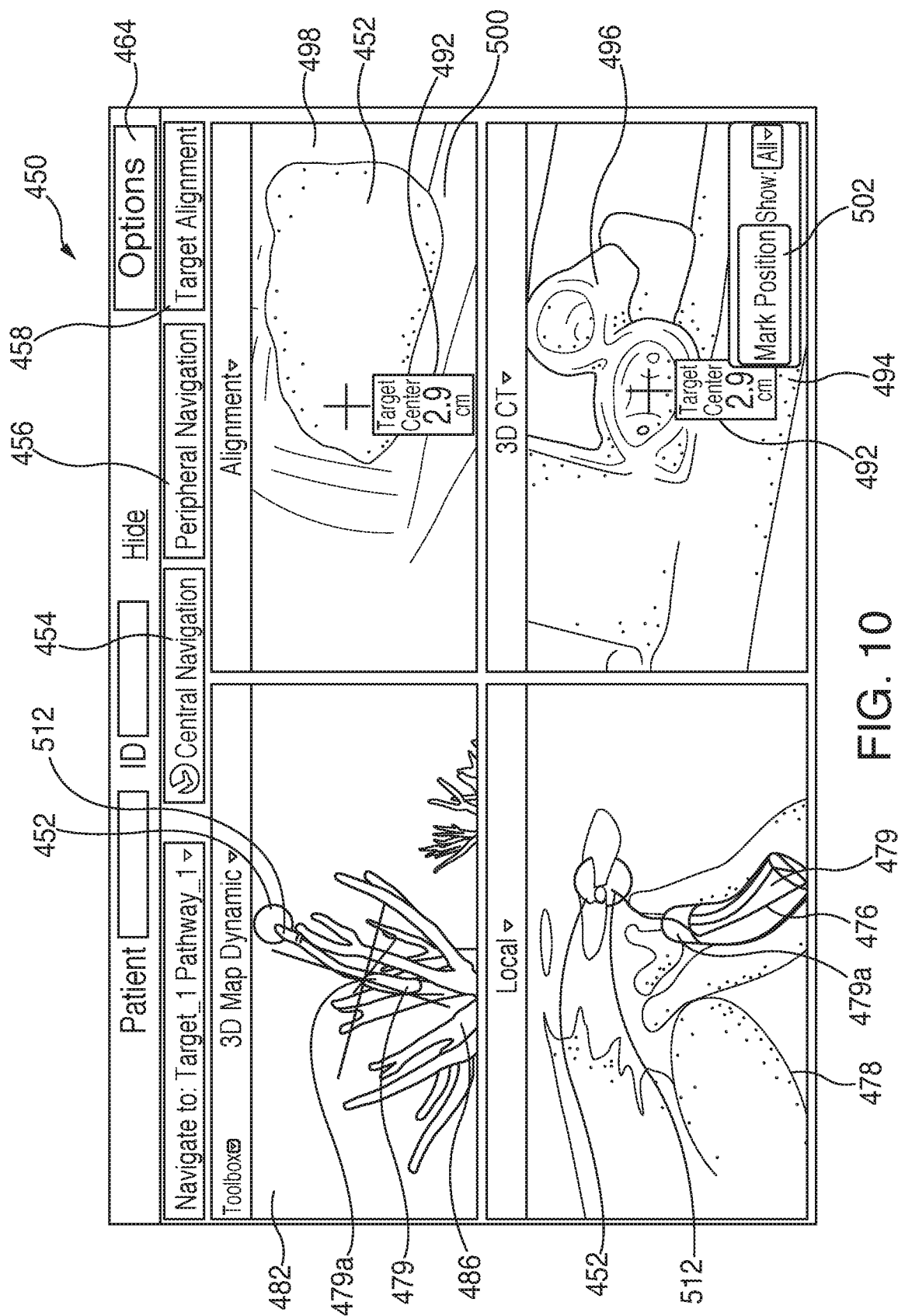
FIG. 10 is an illustration of the view of FIG. 7 further presenting a target alignment tab.

Each tab 454, 456, and 458 includes a number of windows 462 that assist the clinician in navigating to the target. The number and configuration of windows 462 to be presented is configurable by the clinician prior to or during navigation through the activation of an "options" button 464. The view displayed in each window 462 is also configurable by the clinician by activating a display button 466 of each window 462. For example, activating the display button 466 presents the clinician with a list of views for selection by the clinician including a bronchoscope view 470 (FIG. 7), virtual bronchoscope view 472 (FIG. 7), local view 478 (FIG. 8), MIP view (not explicitly shown), 3D map dynamic view 482 (FIG. 7), 3D map static view (not explicitly shown), sagittal CT view (not explicitly shown), axial CT view (not shown), coronal CT view (not explicitly shown), tip view 488 (FIG. 8), 3D CT view 494 (FIG. 10), and alignment view 498 (FIG. 10).

Bronchoscope view 470 presents the clinician with a real-time image received from the bronchoscope 50, as shown, for example, in FIG. 7. Bronchoscope view 470 allows the clinician to visually observe the patient's airways in real-time as bronchoscope 50 is navigated through the patient's airways toward target 452.

Virtual bronchoscope view 472 presents the clinician with a 3D rendering 474 of the walls of the patient's airways generated from the 3D volume of the loaded navigation plan, as shown, for example, in FIG. 7. Virtual bronchoscope view 472 also presents the clinician with a navigation pathway 476 providing an indication of the direction along which the clinician will need to travel to reach the target 452. The navigation pathway 476 may be presented in a color or shape that contrasts with the 3D rendering 474 so that the clinician may easily determine the desired path to travel.

Figure 8:
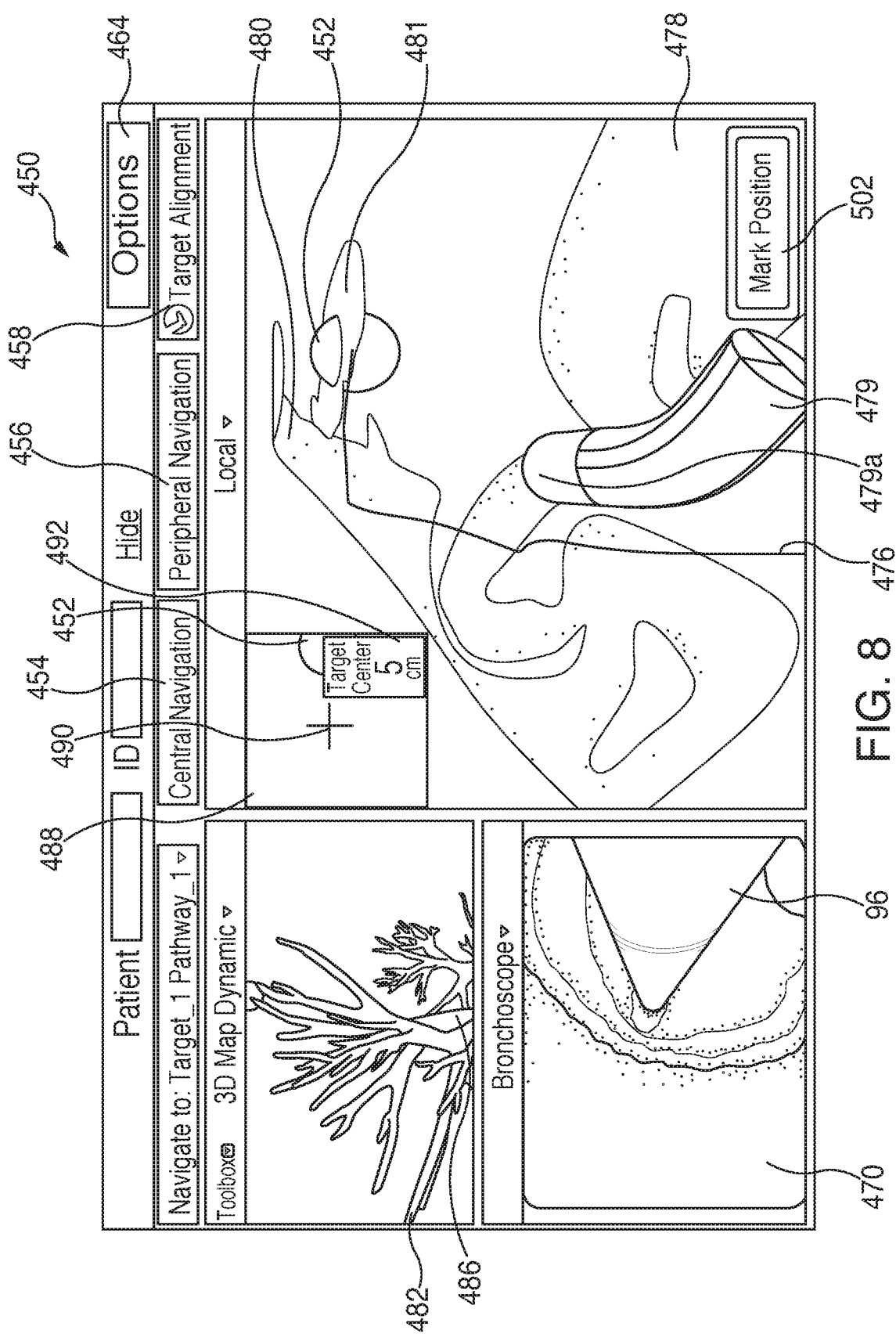
FIG. 8 is an illustration of the view of FIG. 7 further presenting a peripheral navigation tab.

Local view 478, shown in FIG. 8, presents the clinician with a slice 480 of the 3D volume located at and aligned with the distal tip 93 of LG 92. Local view 478 shows target 452, navigation pathway 476, and surrounding airway branches overlaid on slice 480 from an elevated perspective. The slice 480 that is presented by local view 478 changes based on the location of EM sensor 94 relative to the 3D volume of the loaded navigation plan. Local view 478 also presents the clinician with a visualization of the distal tip 93 of LG 92 in the form of a virtual probe 479. Virtual probe 479 provides the clinician with an indication of the direction that distal tip 93 of LG 92 is facing so that the clinician can control the advancement of the LG 92 in the patient's airways. For example, as the clinician manipulates the handle 91 of the catheter guide assembly 90,100, the EWC 96 and the LG 92 locked into position relative thereto rotate, and the orientation of the distal end 479a of virtual probe 479 also rotates relative to the displayed slice 480 to allow the clinician to guide the LG 92 and EWC 96 through the patient's airways. The local view 478 also provides the clinician with a watermark 481 that indicates to the clinician the elevation of the target 452 relative to the displayed slice. For example, as seen in FIG. 8, the majority of the target 452 is located below watermark 481 and may, for example, be displayed as having a dark color such as a dark green, while a smaller portion of target 452 located above watermark 481 may be displayed, for example, as having a light color such as a light green. Any other color scheme which serves to indicate the difference between the portion of target 452 disposed above watermark 481 and the portion of target 452 disposed below watermark 481 may alternatively be used.

The MIP view (not explicitly shown), also known in the art as a Maximum Intensity Projection view is a volume rendering of the 3D volume of the loaded navigation plan. The MIP view presents a volume rendering that is based on the maximum intensity voxels found along parallel rays traced from the viewpoint to the plane of projection. For example, the MIP view enhances the 3D nature of lung nodules and other features of the lungs for easier visualization by the clinician.

3D map dynamic view 482 (FIG. 8) presents a dynamic 3D model 484 of the patient's airways generated from the 3D volume of the loaded navigation plan. Dynamic 3D model 484 includes a highlighted portion 486 indicating the airways along which the clinician will need to travel to reach target 452. The orientation of dynamic 3D model 484 automatically updates based on movement of the EM sensor 94 within the patient's airways to provide the clinician with a view of the dynamic 3D model 484 that is relatively unobstructed by airway branches that are not on the pathway to the target 452. 3D map dynamic view 482 also presents the virtual probe 479 to the clinician as described above where the virtual probe 479 rotates and moves through the airways presented in the dynamic 3D model 484 as the clinician advances the LG 92 through corresponding patient airways.

3D map static view (not explicitly shown) is similar to 3D map dynamic view 482 with the exception that the orientation of the static 3D model does not automatically update. Instead, the 3D map static view must be activated by the clinician to pan or rotate the static 3D model. The 3D map static view may also present the virtual probe 479 to the clinician as described above for 3D map dynamic view 482.

The sagittal, axial, and coronal CT views (not explicitly shown) present slices taken from the 3D volume of the loaded navigation plan in each of the coronal, sagittal, and axial directions. Examples of the coronal, sagittal, and axial CT views can be found in U.S. patent application Ser. Nos. 13/838,805 mentioned above.

Tip view 488 presents the clinician with a simulated view from the distal tip 93 of LG 92, as shown, for example, in FIG. 8. Tip view 488 includes a crosshair 490 and a distance indicator 492. Crosshair 490 may be any shape, size, or color that indicates to the clinician the direction that the distal tip 93 of LG 92 is facing. Distance indicator 492 provides the clinician with an indication of the distance from the distal tip 93 of LG 92 to the center of target 452. Tip view 488 may be used to align the distal tip 93 LG 92 with the target 452.

3D CT view 494 (FIG. 10) presents the clinician with a 3D projection 496 of the 3D volume located directly in front of the distal tip of LG 92. For example, 3D projection 496 presents high density structures such as, for example, blood vessels, and lesions to the clinician. 3D CT view 494 may also present distance indicator 492 to the clinician as described above for tip view 488.

Alignment view 498 (FIG. 10) presents the clinician with a 2D projection 500 of the 3D volume located directly in front of the distal tip 93 of LG 92, for example, as shown in FIG. 10. 2D projection 500 presents high density structures such as, for example, blood vessels and lesions. In 2D projection 500, target 452 may presented as a color, for example, green, and may be translucent. Alignment view 498 may also present distance indicator 492 to the clinician as described above for tip view 488.

Navigation to a target 452 will now be described:

Initially, in step S316, view 450 is presented to the clinician by user interface 202 with central navigation tab 454 active, as shown, for example, in FIG. 7. Central navigation tab 454 may be the default tab upon initialization of view 450 by user interface 202. Central navigation tab 454 presents the clinician with the bronchoscope view 470, virtual bronchoscope view 472, and 3D map dynamic view 482, as described above. Using central navigation tab 452, the clinician navigates bronchoscope 50, LG 92, and EWC 96 toward the target 452 by following the navigation pathway 476 of virtual bronchoscope view 472 along the patient's airways. The clinician observes the progress of bronchoscope 50 in each view 470, 472, and 482. In step S318, the clinician determines whether the airways leading to the target have become too small for bronchoscope 50 and, if so, wedges the bronchoscope 50 in place. Once the bronchoscope 50 has been wedged in place, the clinician activates peripheral navigation tab 456 using input device 210, for example, a mouse or foot pedal, and proceeds to peripheral navigation in step S320.

During peripheral navigation in step S320, peripheral navigation tab 456 is presented to the clinician as shown, for example, in FIG. 8. Peripheral navigation tab 456 presents the clinician with the local view 478, 3D Map Dynamic view 482, bronchoscope view 470, and tip view 488. Peripheral navigation tab 456 assists the clinician with navigation between the distal end of bronchoscope 50 and target 452. As shown in the bronchoscope view 470 in FIG. 8, the clinician extends LG 92 and EWC 96 from the working channel of bronchoscope 50 into the patient's airway toward target 452. The clinician tracks the progress of LG 92, EM sensor 94, and EWC 96 in the local view 478, the 3D map dynamic view 482, and the tip view 488. For example, as described above, and shown in FIG. 8, the clinician rotates LG 92, EM sensor 94, and EWC 96 relative to the patient's airways until the tip 479a of virtual probe 479 is oriented toward the desired airway leading to the target 452. For example, the desired airway may be determined based on the navigation pathway 476 presented in local view 478 and the highlighted portion 486 presented in 3D map dynamic view 482. The clinician then advances LG 92, EM sensor 94, and the EWC 96 into the desired airway and confirms the movement of the EM sensor 94 relative to the target 452 and the patient's airways in the 3D map dynamic view 482 and local view 478. The clinician may also check the location of target 452 on the tip view 488 to determine where the target 452 is relative to the orientation of the distal tip 93 of LG 92 as LG 92 moves closer to the target 452.

Figure 9:
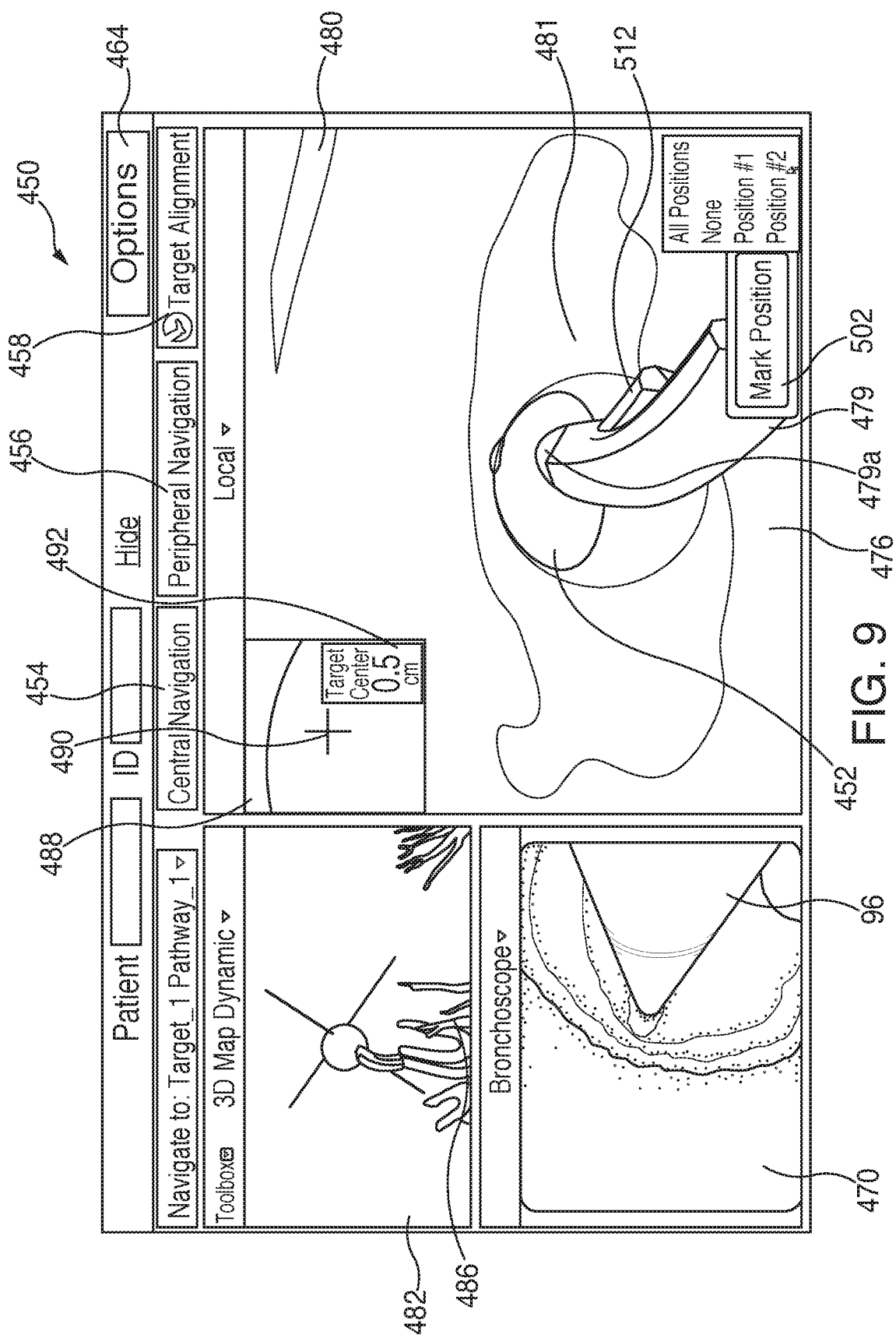
FIG. 9 is an illustration of the view of FIG. 7 further presenting the peripheral navigation tab of FIG. 8 near the target.

When the clinician has advanced the distal tip 93 of LG 92 to target 452, as shown, for example, in FIG. 9, the clinician may decide in step S322 to activate the target alignment tab 458 to confirm target alignment with the target 452.

During target alignment in step S324, target alignment tab 458 is presented to the clinician as shown, for example, in FIG. 10. Target alignment tab 458 presents the clinician with the local view 478, 3D Map Dynamic view 482, 3D CT view 494, and Alignment view 498. Target alignment tab 458 assists the clinician with alignment of the LG 92 with the target 452. By comparing the 3D and 2D projections of the 3D CT view 494 and alignment view 498 with the position and orientation of the virtual probe 479 in the local view 488 and 3D map dynamic view 482, the clinician may make a determination of whether the distal tip 93 of LG 92 is aligned with the target 452 and of the relative distance of the distal tip 93 of LG 92 to the target 452.

After the clinician determines that the target has been aligned in step S326 using the target alignment tab 458, or if the clinician decides not to activate the target alignment view 458 in step S322, the clinician may decide to activate the "mark position" button 502 of either the peripheral navigation tab 456 (FIG. 9) or the target alignment tab 458 (FIG. 10) in step S328 to virtually mark the current position of the virtual probe 479 where the registered position of the virtual probe 479 corresponds to the current location of the distal tip 93 of LG 92. This mark may be permanently recorded as part of the navigation plan to enable a clinician to return to substantially the same location in subsequent navigations or at a later time in the same procedure, for example, where a biopsy sample has been taken and is determined to be cancerous and in need of immediate treatment. More details regarding the process of virtually marking a biopsy location are set forth in U.S. Patent Application No. 62/020,177, entitled METHODS FOR MARKING BIOPSY LOCATION, filed on Jul. 2, 2014, by Brown, the entire contents of which is incorporated herein by reference.

Figure 11:
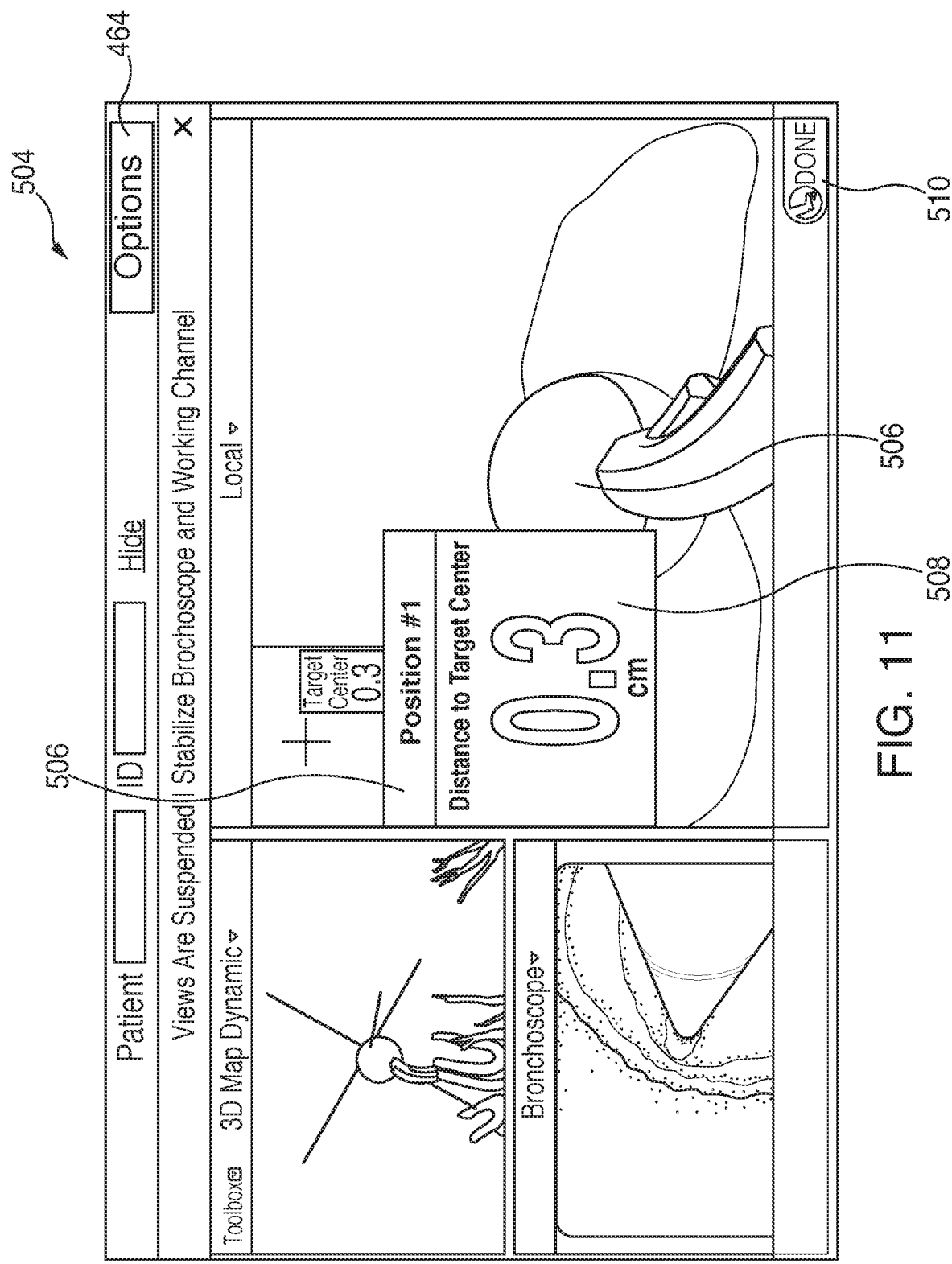
FIG. 11 is an illustration of the user interface of the workstation of FIG. 2 presenting a view for marking a location of a biopsy or treatment of the target.

Once the clinician has activated the "mark position" button 502, the user interface 216 presents the clinician with a view 504 providing the clinician with details of the marked position of the virtual probe 470, as shown, for example, in FIG. 11. For example, view 504 provides the clinician with a biopsy or treatment position number 506 and distance to target center 508 for the clinicians review. While view 504 is presented, the clinician may withdraw the LG 92 from EWC 96 of the bronchoscope 50 and insert a tool through EWC 96 in step S330, for example, a biopsy device 102, a fiducial marking device, an ablation probe, a chemical treatment probe, or other similar tools to sample, mark and/or treat the target 452. Once the clinician has finished sampling, marking, and/or treating the target 452 using the tool, the clinician withdraws the tool from bronchoscope 50 and inserts LG 92 back into bronchoscope 50. The clinician then activates the "done" button 510 to finish marking the target 452.

Once the "done" button 506 has been activated, the user interface 216 presents the clinician with view 500 with one of tabs 454, 456, or 458 active. As can be seen in FIG. 10, for example, a representation of a virtual marker 512 is presented by target alignment tab 458 in various views including, for example, the 3D Map Dynamic view 482, local view 488, or any other view described above to indicate to the clinician the location of a previous treatment site. The clinician then determines whether an additional biopsy, marking, or treatment is required for the target 452 in step S332. If additional biopsies are required, the clinician repeats steps S320 through S330. Because the clinician has already navigated to the target 452, the clinician may alternatively repeat only a subset of steps S320 through S330. For example, the clinician may return to the target alignment tab 458 without activating the peripheral navigation tab 456 to continue navigating to the target or aligning the LG 92 with the target for an additional biopsy, marking, or treatment. Alternatively, the clinician may use only the peripheral navigation tab 456 to continue navigating to the target 452 for an additional biopsy or treatment.

If no additional biopsies or treatments are required, the clinician determines whether there is an additional target planned for navigation by activating the target selection button 460 in step S334. If an additional target is planned for navigation, the clinician activates the additional target and repeats steps S316 through S332 to navigate to the additional target for biopsy or treatment. If the additional target is in the same lung lobe or region as target 452, the clinician may alternatively only repeat a subset of steps S316 through S332. For example, the clinician may start navigation to the additional target using the peripheral navigation tab 456 (step S320) or the target alignment tab 458 (step S324) without using the central navigation tab 454 (step S316) where the location of the wedged bronchoscope 50 can still provide access to the additional target.

If there are no other targets, the clinician has finished the navigation procedure and may withdraw the LG 92, EWC 96, and bronchoscope 50 from the patient. The clinician may then export a record of the navigation procedure in step S336 to memory 202, to a USB device via output module 212, or to a server or other destination for later review via network interface 208.

During the navigation procedure, the EM sensor 94 of LG 92 may continuously update workstation 80 with registration information such that the registration is continuously updated. In addition, workstation 80 may automatically adjust the registration when the registered location of EM sensor 94 of LG 92 in the 3D volume is found to be located outside of an airway of the 3D volume such that EM sensor 94 of LG 92 is reregistered to be within an airway of the 3D volume. For example, the registration may be updated such that the location of the EM sensor 94 in the 3D volume is automatically snapped to the nearest airway. In this manner a dynamic registration of the location of EM sensor 94 of LG 92 relative to the 3D volume of the loaded navigation plan may be accomplished.

Figure 12:
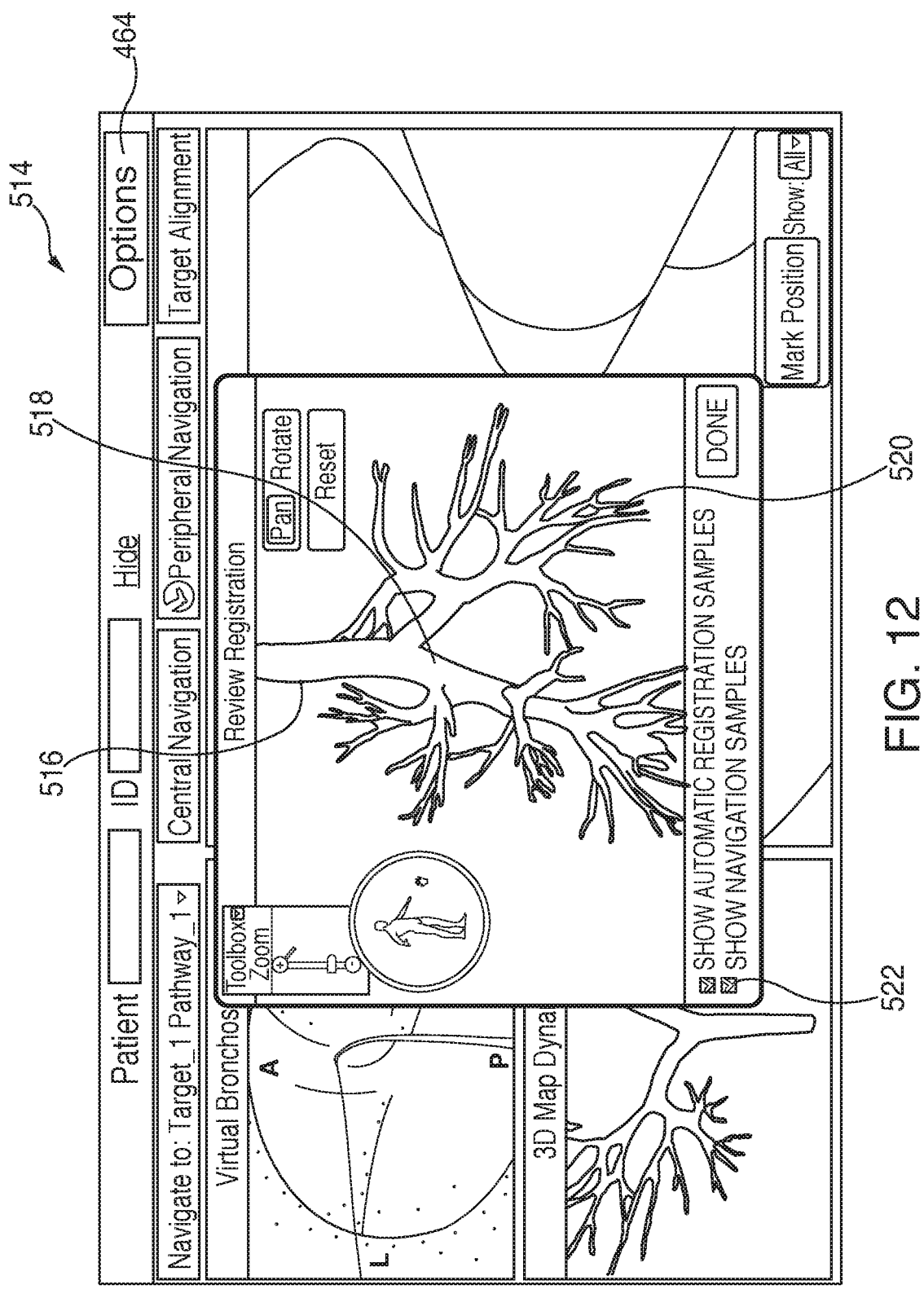
FIG. 12 is an illustration of the user interface of the workstation of FIG. 2 presenting a view for reviewing aspects of registration.

At any time during the navigation procedure the clinician may also review the registration by activating the "options" button 464 and activating a review registration button (not shown). The user interface 216 then presents the clinician with a view 514 as shown, for example, in FIG. 12. View 514 presents the clinician with a 3D model 516 of the patient's bronchial tree generated from the 3D volume of the loaded navigation plan for review of the registration. As shown in FIG. 12, 3D model 516 includes a set of data points 518 that are generated during registration based on the locations to which the sensor 94 of LG 92 has traveled within the patient's airways. The data points 518 are presented on the 3D model 516 to allow the clinician to assess the overall registration of the 3D model 516 with the patient's airways. In addition, during navigation to target 452, a second set of data points 520 are generated based on the locations to which the sensor 94 of LG 92 has traveled on its path to the target 452. Data points 518 and 520 may be color coded, for example, green and purple, respectively, or may have different shapes or other identifying features that allow the clinician to differentiate between data points 518 and 520. The clinician may also activate or de-activate check boxes 522 to control which sets of data points 518 and 520 are presented in the 3D model 516.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for navigating to a target through a patient's bronchial tree, the method comprising:
   loading a navigation plan;
   receiving position information from a location sensor coupled to a probe insertable into a working channel of a bronchoscope and configured to be navigated through the patient's bronchial tree;
   generating a central navigation view including a plurality of views for navigating the bronchoscope through central airways of the patient's bronchial tree toward the target based at least in part on the position information received from the location sensor;
   generating a peripheral navigation view including a plurality of views for navigating the probe through peripheral airways of the patient's bronchial tree to the target based at least in part on the position information received from the location sensor;
   generating a target alignment view including a plurality of views for aligning a distal tip of the probe with the target based at least in part on the position information received from the location sensor; and
   displaying the central navigation view, the peripheral navigation view, or the target alignment view, wherein at least one of the central navigation view, the peripheral navigation view, or the target alignment view includes a local view including:
      a display of a 2D slice from a plurality of 2D slices of a 3D volume, the 2D slice displayed horizontally within a 3D window and selected from the plurality of 2D slices based on a current orientation of a longitudinal axis of the probe and the position information received from the location sensor, a position of the 2D slice within the 3D window changing based on a change in the position information received from the location sensor;
      a virtual representation of the probe overlaid onto the 2D slice in the 3D window, the virtual representation of the probe being fixed relative to the 3D window as the display of the 2D slice changes;
      a 3D representation of the target displayed relative to the 2D slice in the 3D window, the 3D representation of the target including an upper portion of the target located above the 2D slice within the 3D window and a lower portion of the target located below the 2D slice within the 3D window; and
      a watermark displayed against the 3D representation of the target in the 3D window.

2. The method according to claim 1, wherein each of the central navigation view, peripheral navigation view, and target alignment view are configured to present one or more views selected from the group consisting of a bronchoscope view, a virtual bronchoscope view, a local view, a MIP view, a 3D map dynamic view, a 3D map static view, a sagittal CT view, an axial CT view, a coronal CT view, a tip view, a 3D CT view, and an alignment view.

3. The method according to claim 2, wherein the central navigation view is configured to present the bronchoscope view, virtual bronchoscope view, and 3D map dynamic view.

4. The method according to claim 2, wherein the peripheral navigation view is configured to present the bronchoscope view, 3D map dynamic view, tip view, and local view.

5. The method according to claim 2, wherein the target alignment view is configured to present the 3D map dynamic view, local view, alignment view, and 3D CT view.

6. The method according to claim 2, wherein the 3D map dynamic view includes a 3D model of the patient's bronchial tree, the 3D map dynamic view configured to automatically adjust the orientation of the 3D model in response to movement of the location sensor within the patient's bronchial tree.

7. The method according to claim 6, wherein the 3D model includes a highlighted portion indicating a pathway through the patient's bronchial tree to the target.

8. The method according to claim 2, wherein at least one of the 3D map dynamic view or the local view includes a virtual representation of the distal tip of the probe, the virtual representation configured to provide an indication of an orientation of the distal tip of the probe.

9. The method according to claim 8, wherein the distal tip of the probe defines a configuration selected from the group consisting of a linear, a curved, or an angled configuration, and wherein the virtual representation of the distal tip of the probe has the same configuration as the distal tip of the probe.

10. The method according to claim 8, wherein at least one of the 3D map dynamic view or the local view is configured to adjust the orientation of the virtual representation of the distal tip of the probe in response to a change in orientation of the distal tip of the probe within the patient's airways.

11. The method according to claim 2, wherein the virtual bronchoscope view includes a virtual pathway configured to provide an indication of a pathway leading toward the target.

12. A method for navigating a probe to a target through a patient's bronchial tree, the method comprising:
    displaying a central navigation view for navigating a bronchoscope through central airways of the patient's bronchial tree toward the target;
    displaying a peripheral navigation view for navigating the probe through peripheral airways of the patient's bronchial tree to the target based at least in part on position information of the probe; and
    displaying a target alignment view for aligning a distal tip of the probe with the target based at least in part on the position information of the probe, wherein at least one of the central navigation view, the peripheral navigation view, or the target alignment view includes a local view including:
       a display of a 2D slice from a plurality of 2D slices of a 3D volume, 2D slice displayed horizontally within a 3D window and selected from the plurality of 2D slices based on a current orientation of a longitudinal axis of the probe and the position information of the probe, position of the 2D slice within the 3D window changing based on a change in the position information the probe;
       a virtual representation of the probe overlaid onto the 2D slice in the 3D window, the virtual representation of the probe being fixed relative to the 3D window as the display of the 2D slice changes;
       a 3D representation of the target displayed relative to the 2D slice in the 3D window, the 3D representation of the target including an upper portion located above the 2D slice within the 3D window and a lower portion located below the 2D slice within the 3D window; and a watermark displayed against the 3D representation of the target in the 3D window.

13. The method according to claim 12, further comprising displaying a 3D map dynamic view including a 3D model of the patient's bronchial tree.

14. The method according to claim 13, further comprising automatically adjusting an orientation of the 3D model in response to a change in the position information of the probe.

15. A method for navigating a probe to a target through a patient's bronchial tree, the method comprising:
 displaying a peripheral navigation view for navigating the probe through peripheral airways of the patient's bronchial tree to the target based at least in part on position information of the probe; and
 displaying a target alignment view for aligning a distal tip of the probe with the target based at least in part on the position information of the probe, wherein at least one of the peripheral navigation view or the target alignment view includes a local view including:
  a display of a 2D slice from a plurality of 2D slices of a 3D volume, the 2D slice displayed horizontally within a 3D window and selected from the plurality of 2D slices based on a current orientation of a longitudinal axis of the probe and the position information of the probe, a position of the 2D slice within the 3D window changing based on a change in the position information the probe;
  a virtual representation of the probe overlaid onto the 2D slice in the 3D window, the virtual representation of the probe being fixed relative to the 3D window as the display of the 2D slice changes;
  a 3D representation of the target displayed relative to the 2D slice in the 3D window, the 3D representation of the target including an upper portion located above the 2D slice within the 3D window and a lower portion located below the 2D slice within the 3D window; and
  a watermark displayed against the 3D representation of the target in the 3D window.

16. The method according to claim 15, further comprising:
 displaying a 3D map dynamic view including a 3D model of the patient's bronchial tree; and
 automatically adjusting an orientation of the 3D model in response to a change in the position information of the probe.

17. The method according to claim 1, wherein at least one of the central navigation view, the peripheral navigation view, or the target alignment view includes an indication of a distance between the probe and the target.

18. The method according to claim 12, wherein at least one of the central navigation view, the peripheral navigation view, or the target alignment view includes an indication of a distance between the probe and the target.

19. The method according to claim 15, wherein at least one of the peripheral navigation view or the target alignment view includes an indication of a distance between the probe and the target.

* * * * *